United States Patent [19]

Ogata et al.

[11] Patent Number: 5,797,872
[45] Date of Patent: Aug. 25, 1998

[54] METHOD OF TREATING DOMESTIC ANIMALS SUCH AS COWS FOR MASTITIS AND APPARATUS FOR INJECTING OZONE INTO BREASTS

[75] Inventors: Atsuya Ogata, Hokkaido; Shigeru Suzuki, Kanagawa, both of Japan

[73] Assignee: Nippon Ozone Co., Ltd., Tokyo, Japan

[21] Appl. No.: 858,155

[22] Filed: Apr. 4, 1997

[30] Foreign Application Priority Data

Apr. 26, 1996 [JP] Japan ................................ 8-131331
Sep. 12, 1996 [JP] Japan ................................ 8-262282

[51] Int. Cl.⁶ .......................................... A61M 31/00
[52] U.S. Cl. ...................................... 604/49; 604/25
[58] Field of Search .......................... 604/30, 25, 49, 604/48, 65–67, 118, 246

Primary Examiner—Manuel Mendez
Attorney, Agent, or Firm—Rogers & Killeen

[57] ABSTRACT

Disclosed are a method and an apparatus for use in the method for treating cow's mastitis by means of quite a different novel chemotherapy without relying on drugs such as existing antibiotics. In order to inject ozone through a teat orifice 17 of a breast 18 into the interior of the breast 18, an ozone injecting apparatus 1 comprises an ozone generator 5 connected to an oxygen cylinder 2 or an air compressor; an ozone guide tube 13 for guiding ozone generated by the ozone generator 1; and an ozone injection nozzle 14 fitted to the tip of the guide tube 13 and intended to be inserted into the teat orifice 17.

13 Claims, 6 Drawing Sheets

METHOD OF TREATING DOMESTIC ANIMALS SUCH AS COWS FOR MASTITIS AND APPARATUS FOR INJECTING OZONE INTO BREASTS

BACKGROUND OF THE INVENTION

1. Field of the Invention

The present invention relates to a method and an apparatus for use therein, providing a simple and safe treatment for domestic animals's mastitis, which is a serious threat to dairy farming for breeding domestic animals such as cows, goats, pigs, etc.

2. Description of the Related Art

In order to treat, e.g., cows's mastitis, a dosage of antibiotics has hitherto been typically performed. More specifically, the antibiotics continued to be injected into breasts over a few days to a week and if necessary, the antibiotics were injected into muscles, veins, or arteries, merely for the purpose of suppressing a propagation of disease-causing bacteria residing within the breasts, mammary cisterns or teats, to thereby treat the mastitis.

However, the conventional treatment taking antibiotics has resulted in curing rate and therapeutic effect which are not necessarily so high and entailed the following deficiencies.

(1) Drug cost becomes high.

(2) A long-term treatment period is needed.

(3) Specialized knowledge and diagnostic techniques are required for the selection of drugs, with a further need for higher skills depending on the drug dosing path.

(4) There is a need for a further expensive drug to supplementarily enhance the spontaneous curing abilities of the cow since the antibiotics merely have a function to suppress a propagation of the bacteria.

(5) It is difficult for the antibiotics to reach deep regions of the breast since the amount of the injected antibiotics is small, and the stimulation may bring about a damage to tissues.

(6) It does not allow for the processing of toxin produced by the infected microbes in the inflaming tissues and for the processing of free radicals caused by the inflammation.

(7) There appear resistant bacteria and superinfection due to common use of the antibiotics.

(8) Due to the antibiotics remaining in the products, milk of the cow under treatment must be dumped until the time when remainder is no longer observed, resulting in a loss attendant on treatment.

(9) The antibiotics are drugs requiring direction from a veterinary surgeon, so that they can be used only under the direction from the veterinary surgeon.

(10) Operator must remain in close vicinity to the infected cow for treatment and hence may be subjected to an unexpected danger due to a sudden irritation of the cow.

SUMMARY OF THE INVENTION

In view of the above problems involved in the conventional treatment method, the present invention aims to provide a method of treating cow's mastitis by means of quite a different novel chemotherapy without need to rely on drugs such as antibiotics, and an apparatus for use in this method.

According to a first aspect of the present invention which was conceived in order to overcome the above problems, there is provided a method of treating domestic animals such as cows for mastitis, comprising the step of injecting ozone through a teat orifice of a breast into the interior of the breast. More specifically, the present invention provides a novel treatment method based on a technical idea in which ozone is caused to act on disease-causing microbes residing within the breast, mammary cistern and teat orifice and on their tissues. The present invention has succeeded in safely and effectively injecting ozone into the breast, achieving a rapid cure of mastitis and solving the above problems.

According to a second aspect of the present invention, in order to carry out the above method, there is provided an ozone injecting apparatus for breasts, comprising an ozone generator connected to an oxygen cylinder or an air compressor; an ozone guide tube for guiding ozone generated by the ozone generator; and an ozone injection nozzle fitted to the tip of the guide tube and intended to be inserted into a teat orifice.

According to a third aspect of the present invention, there is provided an ozone injecting apparatus for breasts, comprising an ozone generator connected to an oxygen cylinder or an air compressor and including a gas flow passage; and a four-way valve disposed in the gas flow passage, the four-way valve being associated with an ozone decomposer and an ozone guide tube, the guide tube having at its tip an ozone injection nozzle intended to be inserted into a teat orifice of a cow.

In the ozone injecting apparatus, the switching valve may further be associated with an ozone analyzer for automatically measuring and displaying a density of ozone generated by the ozone generator. The density to be displayed by the ozone analyzer may be appropriately regulated so as to be able to constantly effect an injection of ozone having a proper density.

Preferably, prior to generation of ozone, the ozone generator flows a material gas for a predetermined duration to discharge air remaining within the generator and the gas guide tube.

In the apparatus of the present invention, to ensure a generation of clean ozone, the ozone generator may further include a discharge electrode made of a material such as glass, quartz, ceramics or a metal coated with ceramics to suppress a generation of metal ions and metal dusts, metal dusts.

In the apparatus of the present invention, the ozone injection nozzle is preferably a hollow pipe having a diameter allowing an insertion into a teat orifice of a cow, the pipe having at its distal end a multiplicity of minute ozone jet orifices. Alternatively, the ozone injection nozzle may be a hollow pipe having a diameter allowing an insertion into a teat orifice of a cow, the pipe having at its distal end a gas filter for jetting ozone.

The gas volume of ozone and oxygen to be injected into a breast at a time is preferably 0.1 to 3 liter. This is due to the fact that the amount of ozone less than 0.1 liter is too small and hence it is not expected to present a satisfactory therapeutic effect, whereas the amount of ozone more than 3 liters confers too great a load onto breasts. The density of ozone to be injected is preferably 1 to 50 mgO$_3$/liter. This is due to the fact that for the density of 1 mgO$_3$/liter or less the ozone is decomposed before it reaches the injection nozzle, making it difficult to present a satisfactory effect, whereas for the density of 50 mg/liter or more the ozone disadvantageously acts on the living tissues.

Although the above injecting apparatus ensures a certain effect on treatment for mastitis by injecting ozone into the cow's breast, it does not particularly allow for the pressure of injection when the ozone is ozone injection pressure.

Thus, the present invention provides an apparatus for injecting ozone into a cow's breast, having a simple construction, easy to operate, and capable of injecting a clean and appropriate density of ozone under an appropriate pressure by way of a cow's teat orifice into the breast, as well as capable of coping with an increase in the ozone injection pressure.

According to a fourth aspect of the present invention, there is provided an ozone injecting apparatus for breasts, ensuring an ozone injection under appropriate pressure conditions described hereinabove, the apparatus comprising an oxygen supplier; an ozone generator for receiving oxygen supplied from the oxygen supplier to generate ozone and for discharging the ozone, the ozone generator including an ozone delivery flow passage; a flow rate control valve disposed in the ozone delivery flow passage for controlling the flow rate of ozone; a discharge control valve disposed in the ozone delivery flow passage for discharging surplus ozone to the outside; an ozone guide tube coupled to the flow rate control valve and having at its tip an ozone injection nozzle for injecting ozone into a cow's breast; and a pressure detector disposed in the ozone guide tube for detecting a pressure of ozone injected into the cow's breast; the flow rate control valve being controlled on the basis of a detection value of the pressure detector so as to discharge surplus ozone through the discharge control valve.

This ozone injecting apparatus may further comprise an ozone decomposer coupled to the discharge control valve disposed in the ozone delivery flow passage, the ozone decomposer serving, when a pressure detected by the pressure detector exceeds a predetermined level, to allow surplus ozone to flow thereinto and to be decomposed and converted into oxygen. Safety is thus secured.

Preferably, the ozone injecting apparatus further comprises a check valve disposed in the ozone guide tube short of the ozone injection nozzle, thereby preventing milk reservoiring within the mammary cistern from backward flowing, to prohibit the ozone flow passage from being contaminated by the backward flowing of the milk, thus always effecting a clean ozone injection.

By virtue of the above solution, the treatment method of the present invention ensures a therapeutic effect equal or superior to the conventional treatment method using antibiotics, while realizing an extremely reduced treatment cost because of using oxygen as its material for the generation of ozone. In addition, there is no need for costly and time-consuming diagnostic techniques since the powerful oxidizing action kills all of the disease-causing microbes.

In the treatment method of the present invention, pressurized ozone is injected into the breast to thereby significantly expand extremely narrow and elongated milk vessels located at deep regions, promoting a discharge to the outside of the body, of inflaming products residing at deep regions of the breast and infected milk stored within the mammary cistern. Simultaneously, the supply of oxygen to the inflaming tissues will increase the spontaneous curing abilities which the living bodies of the domestic animals intrinsically possess, which will instantaneously act on noxious free radicals to make them innocuous, enabling the inflammation to be early recovered and the treatment period to be remarkably reduced.

Moreover, the procedure of action is quite different from that of the antibiotics, which will cause no occurrence of resistant bacteria and superinfection. Due to no remainder in the products, unlike the antibiotics, safety requirements for foods are satisfied resulting in no dumping of products which was frequent in the conventional treatment, which will contribute to a complete elimination of economical loss attendant on the treatment in the dairy farming.

Ozone serves to kill all of the infected disease-causing microbes without choosing species thereof and to supply oxygen to the damaged inflaming tissues while simultaneously oxidizing and neutralizing toxins produced by such disease-causing microbes. This will enhance the infection-protective and recovery capabilities of the tissues which the domestic animals intrinsically possess, presenting a remarkably therapeutic effect. Due to such a difference in manner of action, the method of treating domestic animals for mastitis of the present invention realizes a remarkable reduction in treatment period whereas the conventional treatment method using antibiotics requires a longer treatment period.

For this reason, there can be omitted bacteriological examinations which were hitherto necessary to identify the disease-causing microbes and to select effective antibiotics, which will result in reduced diagnostic costs as well as no need for special diagnostic techniques. This also means that there is no need to prepare expensive drugs for treatment as in the prior art, since the oxygen is used as a material for the generation of ozone and that a significantly reduced treatment cost is thus achieved.

Furthermore, according to the method of treating cow's mastitis of the present invention, the dairy farming is freed from an inconvenience of dumping the products due to drugs remaining in the milk and meat, which has often taken place as a result of use of the antibiotics. That is, ozone is an extremely unstable substance and if left to stand, will return to oxygen through self-decomposition in a brief period of time. In addition, the instant that the ozone conducts a strong oxidizing action within the breast, it will return to extremely stable initial oxygen and hence no zone is allowed to remain in the products. The economic loss is thus entirely overcome from which the dairy farming has hitherto been suffered due to dumping of products arising from the remaining drugs.

Up to now, the acquisition of intellect of the disease-causing microbes against antibiotics has occurred due to a long-term use of the antibiotics and/or to a selection of the antibiotic having no sensitivity to the disease-causing microbes. In contrast with this, ozone acts on the disease-causing microbes without choosing any species thereof. Dissimilar to the antibiotics which can present an effect only through the action to prohibit the propagation of the disease-causing microbes, ozone exhibits its effects through killing of disease-causing microbes due to its strong oxidizing action, or through oxidizing and neutralizing the noxious toxin produced by the disease-causing microbes, or through supply of oxygen to encourage the infection-protective function and damaged tissue recovery function, that is, spontaneous curing abilities which the living bodies originally possess. This will remarkably reduce the period required for the treatment and hence the disease-causing microbes have no time to acquire the tolerance, resulting in no appearance of resistant bacteria.

BRIEF DESCRIPTION OF THE DRAWINGS

The above and other objects, aspects, features and advantages of the present invention will become more apparent from the following detail description with reference to the accompanying drawings, in which.

DESCRIPTION OF THE PREFERRED EMBODIMENTS

Figure 1:
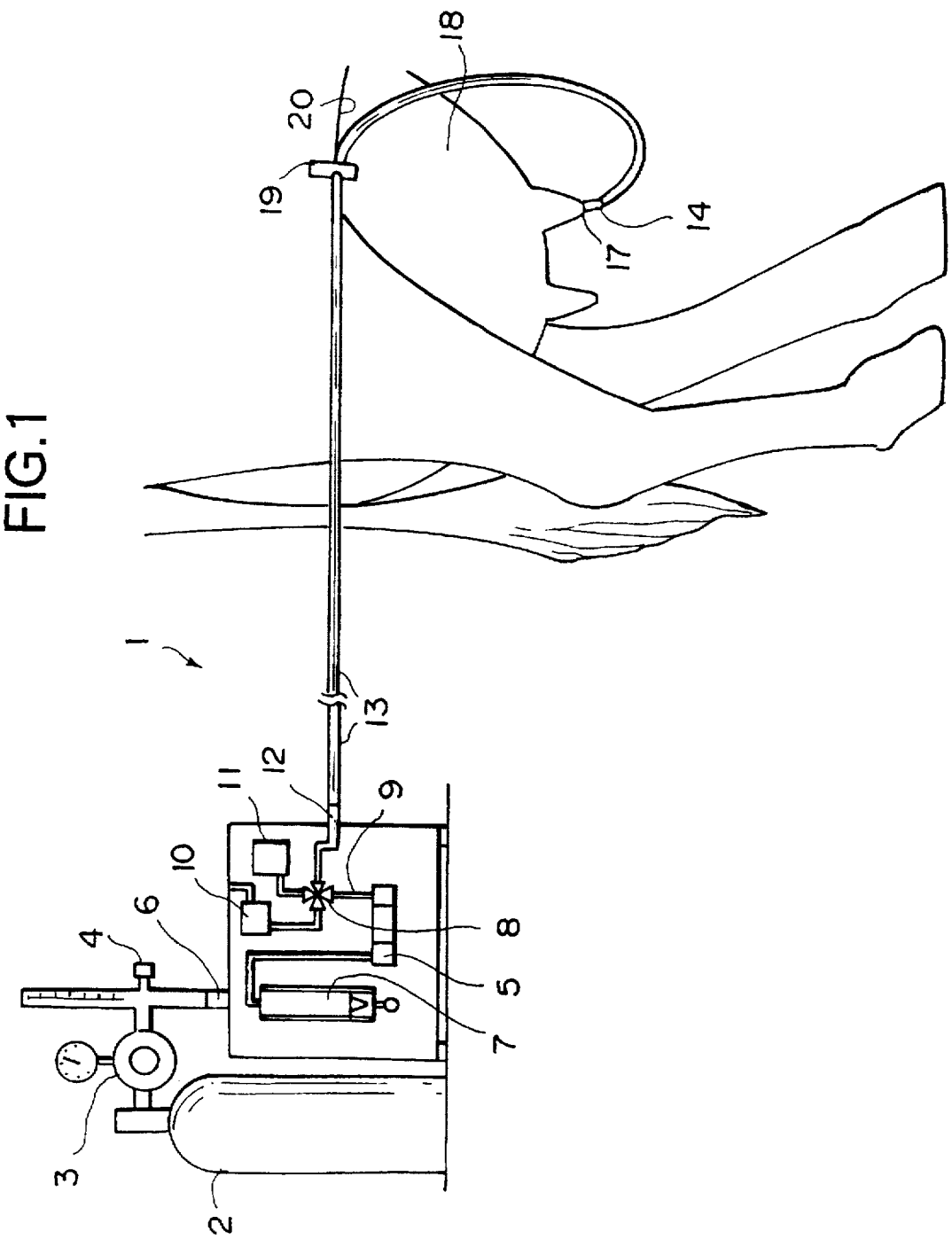
FIG. 1 is a systemic view of an embodiment of an ozone injecting apparatus for breasts in accordance with the present invention.
Figure 2:
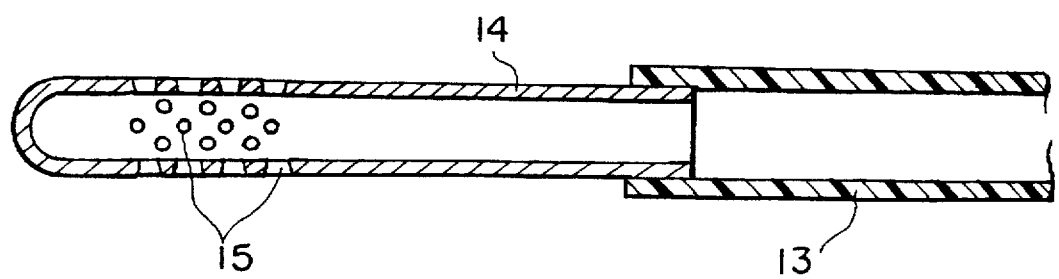
FIG. 2 is a sectional view of an embodiment of an ozone injection nozzle.
Figure 3:
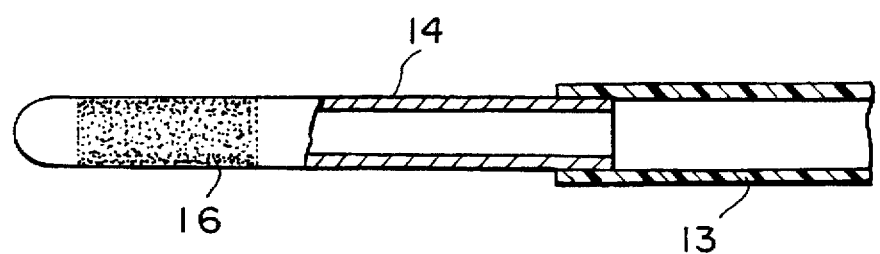
FIG. 3 is a sectional view of another embodiment of the ozone injection nozzle.
Figure 4:
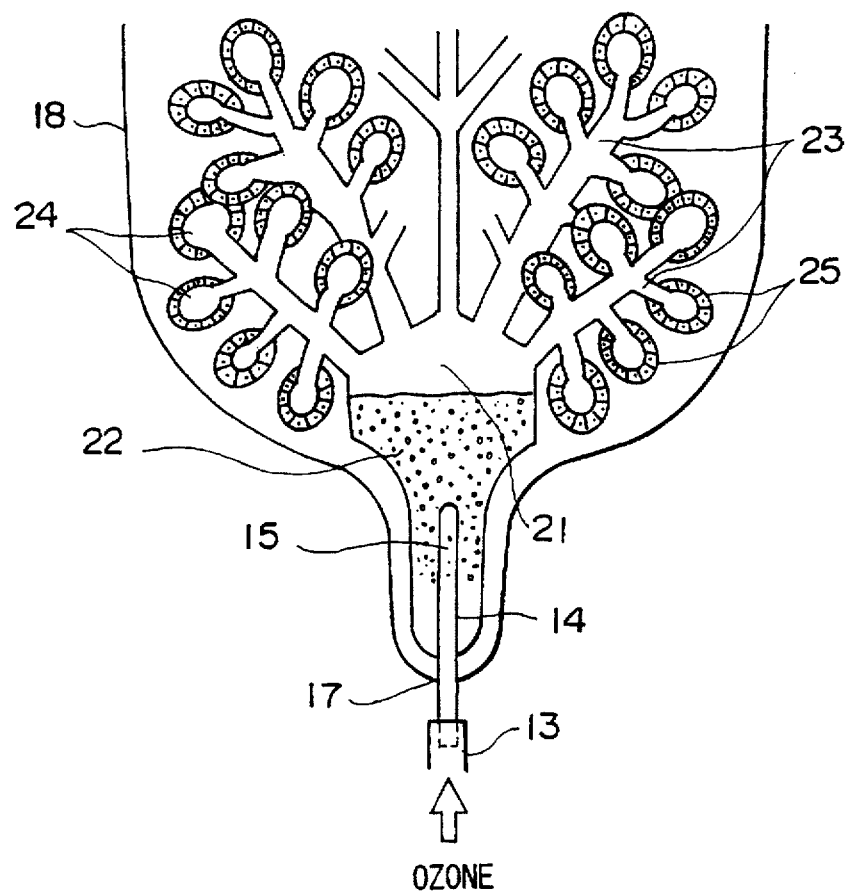
FIG. 4 is a diagrammatic view showing the interior of a breast in use of the apparatus of the present invention.
Figure 5:
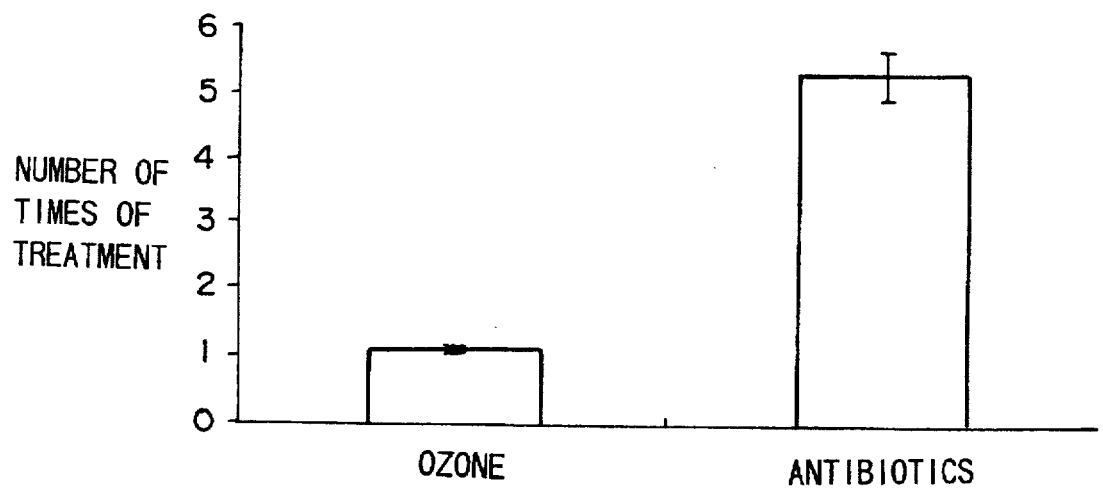
FIG. 5 is a graphic representation showing a therapeutic effect achieved by a method of the present invention.
Figure 6:
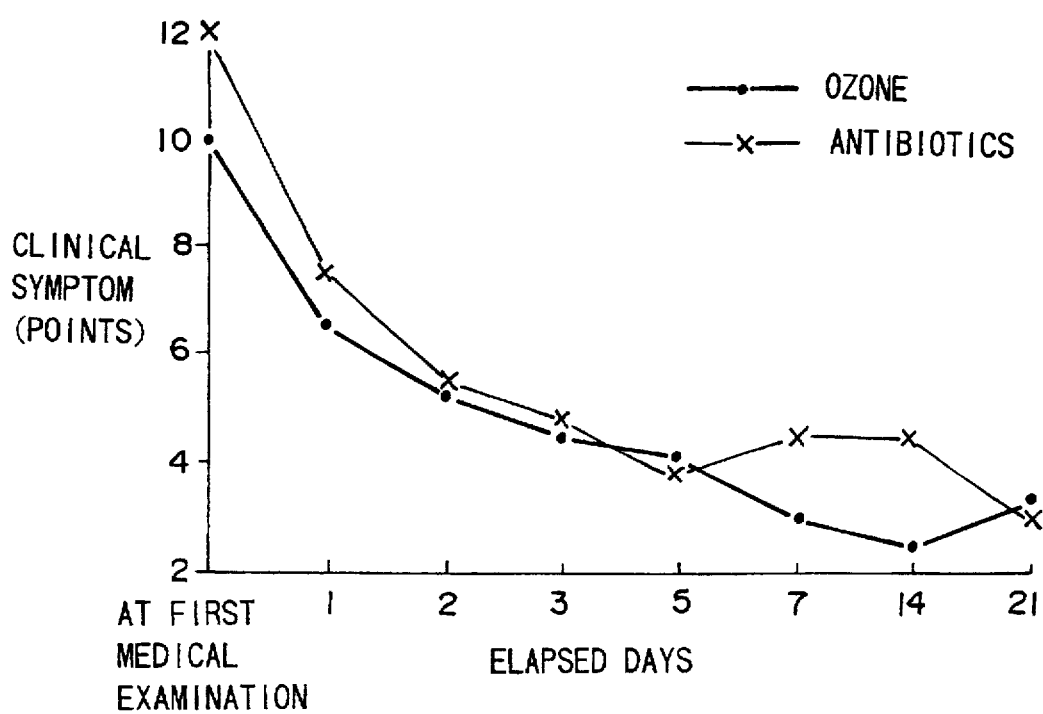
FIG. 6 is a graphic representation showing another therapeutic effect achieved by the method of the present invention.
Figure 7:
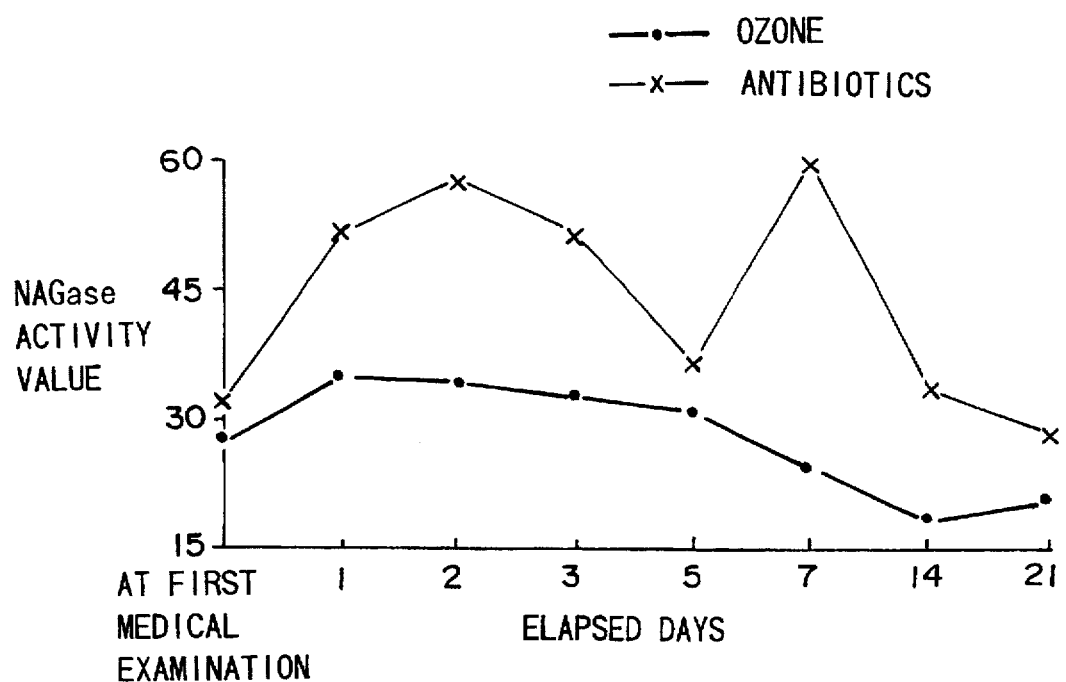
FIG. 7 is a graphic representation showing a further therapeutic effect achieved by the method of the present invention.
Figure 8:
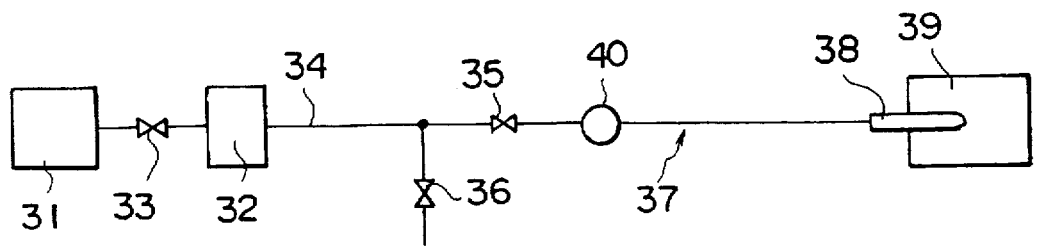
FIG. 8 is a systemic view of another embodiment of the apparatus in accordance with the present invention.
Figure 9:
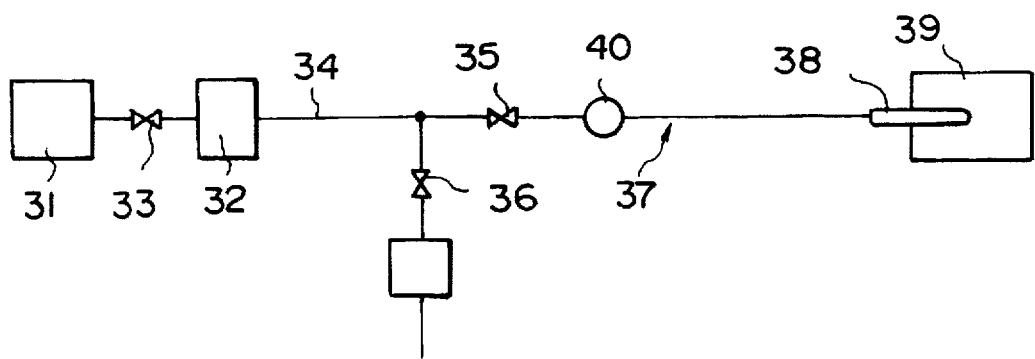
FIG. 9 is a systemic view of a further embodiment of the apparatus.
Figure 10:
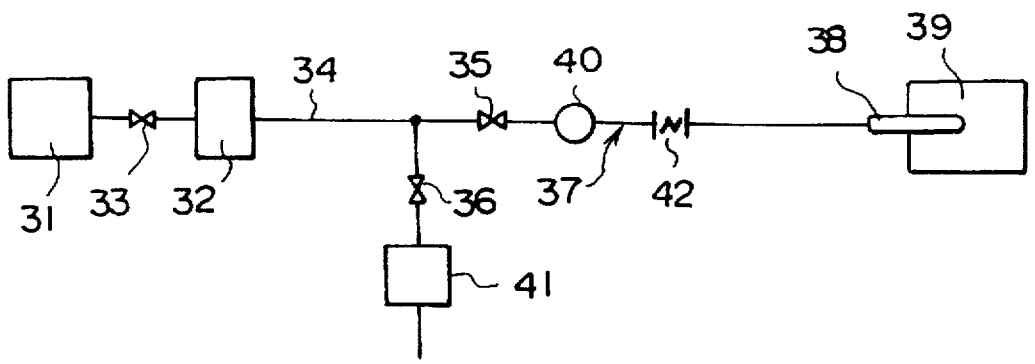
FIG. 10 is a systemic view of a still further embodiment of the apparatus.

An ozone injecting apparatus for breasts in accordance with the present invention will now be described in greater detail with reference to the accompanying drawings which illustrate preferred embodiments thereof in a non-limitative manner. FIG. 1 is a systemic view of an embodiment of the apparatus in accordance with the present invention; FIG. 2 is a sectional view of an embodiment of an ozone injection nozzle; FIG. 3 is a sectional view of another embodiment of the ozone injection nozzle; FIG. 4 is a diagrammatic view showing the state within a breast in use of the apparatus of the present invention; FIG. 5 is a graphic representation showing a therapy achieved by a method of the present invention; FIG. 6 is a graphic representation showing another therapy achieved by the method of the present invention; FIG. 7 is a graphic representation showing a further therapy achieved by the method of the present invention; FIG. 8 is a systemic view of another embodiment of the apparatus in accordance with the present invention; FIG. 9 is a systemic view of a further embodiment of the apparatus; and FIG. 10 is a systemic view of a still further embodiment of the same apparatus.

Referring to FIG. 1, the ozone injecting apparatus for breasts in accordance with the present invention is generally designated at reference numeral 1 and comprises an oxygen cylinder 2, a pressure reducing valve 3 for reducing the pressure inside the oxygen cylinder 2 to keep it at a certain pressure level, a faucet 4, an ozone generator 5 having an oxygen inlet 6, and a flowmeter 7. Oxygen within the oxygen cylinder 2 passes through the pressure reducing valve 3 to be kept to a certain pressure level, and opens the faucet 4 with a predetermined flow rate. The oxygen further flows through the oxygen inlet 6 of the ozone generator 5 and via the flowmeter 7 into the ozone generator 5. The ozone generator 5 serves to convert the thus fed oxygen into ozone by means of silent discharge.

The ozone injecting apparatus 1 further comprises a switching valve in the form of a four-way valve 8 disposed in a flow passage 9 for ozone which has been generated as a result of the conversion in the ozone generator 5, the valve 8 being associated with an ozone decomposer 10 for decomposing the ozonized oxygen generated in the ozone generator 5 into harmless oxygen, an ozone analyzer 11 for sampling a part of the ozone generated in the ozone generator 5 to automatically measure and display a density thereof, and an ozone outlet 12 through which the ozone is fed into an ozone guide tube 13 having at its tip the ozone injection nozzle 14. It is to be appreciated that although the above embodiment employs the ozone analyzer 11 connected to the four-way valve 8 serving as the switching valve, the ozone analyzer 11 is not essential to the present invention but may be provided if necessary.

The ozone guide tube 13 should be a flexible ozone-resistant tube (made of fluorinated rubber, silicone rubber, etc.). The material of the ozone injection nozzle 14 should be a metal having a resistance to oxidization by ozone (stainless steel or aluminum) or ceramics or plastics (vinyl chloride resin, fluororesin).

Referring to FIG. 2 in conjunction with FIG. 4, the ozone injection nozzle 14 is typically formed from a hollow pipe 2 mm in external diameter, 1 mm in internal diameter, 0.5 mm in thickness, and 50 mm in length, with a round and smooth extremity so as to ensure a secure penetration without injuring a teat orifice 17 at the time of insertion thereof. The nozzle 14 includes a multiplicity of minute ozone jet orifices 15 each having a diameter of 0.3 mm and formed in the wall in the region of 10 mm to 25 mm from the extremity. The number of the ozone jet orifices 15 is not particularly restricted, but is typically preferably 20 to 30.

Referring to FIG. 3, there is depicted another embodiment of the ozone injection nozzle 14, which comprises a gas filter 16 including a further multiplicity of more minute ozone jet orifices and fused to the hollow pipe similar to the above. Orifices of the gas filter 16 are typically of diameters of 0.01 to 1.1 μm.

In order to treat a cow for mastitis with the ozone injecting apparatus constructed as set forth hereinabove, the ozone guide tube 13 is first coupled to the ozone outlet 12, and then the ozone injection nozzle 14 is inserted through the teat orifice 17 into the interior of a breast 18. With opening the faucet 4 annexed to the oxygen cylinder 2 and presetting the four-way valve 8 to allow oxygen to flow into the ozone decomposer 10, once the ozone generator 5 is activated, ozone is generated and the ozone analyzer 10 displays a density of the ozone. When the ozone density reaches an appropriate level, the four-way valve 8 is changed over so that the ozone is guided through the guide tube 13 into the injection nozzle 14 and then via the teat orifice 17 and through the ozone jet orifices 15 of the injection nozzle 14 into the breast 18.

Referring back to FIG. 1, a retaining clip 19 is attached to the guide tube 13 so as to retain the guide tube 13 at antero-knee puckers 20 anterior to a cow's hind leg knee. The retaining clip 19 serves to prevent the ozone injection nozzle 14 and the guide tube 13 from coming off without need to hold them by operator's hand during the treatment, and enables the operator to work apart from the cow, thereby ensuring the safety of the operator in case the cow has become disturbed.

When ozone is thus injected into the breast of the cow, infected milk 22 within a mammary cistern 21 can be effectively exposed to ozone as shown in FIG. 4. More specifically, since the ozone injection nozzle 14 includes a multiplicity of minute ozone jet orifices 15, the ozone jet results in fine bubbles so as to increase surface areas sensitized to disease-causing microbes residing within the infected milk 22, thereby allowing the infected milk 22 stored within the mammary cistern 21 to be fully sensitized in a brief period of time. In addition, farther milk vessels 23 and mammary alveolus 24 are fully expanded by a pressure of the injected ozone, so that the ozone is allowed to reach the farthest mammary gland cells 25 while simultaneously urging the inflammation products and infected milk 22 to be discharged, thereby effecting a satisfactory treatment of cow's mastitis.

The apparatus of the present invention is applicable to mastitis including acute mastitis, clinical mastitis and latent mastitis. The present invention can also be applied to a treatment for a dried-up or blinded teat in the same manner as described hereinabove. Apart from the mastitis, the present invention is further applicable to a treatment for intraabdominal infectious disease, urinary tract infectious disease, intrauterine infectious disease and intrablood infectious disease.

The oxygen cylinder 2 shown in FIG. 1 is intended to be used in combination with the ozone generator 5. The cylinder 2 may be carried alone or may be accommodated within a casing together with the other components for use. Alternatively, the oxygen cylinder 2 may be replaced by an air compressor capable of supplying a sufficient pressure to the ozone generator 5, to thereby enable the air to use as the material. Ozone to be injected into the breast 18 can be not only in the form of an ozone gas but in the form of an ozone water obtained by dissolving ozone into water.

In place of the minute ozone jet orifices of the ozone injection nozzle shown in FIG. 2, the hollow pipe may be loaded with air stones so as to be able to form fine ozone bubbles.

Referring to FIGS. 5 to 7 of the accompanying drawings, description will now be given of a method of treating domestic animals' mastitis in accordance with the present invention, and an apparatus for use in the method, on the basis of procedures and results of clinical therapeutic tests.

Pressure controlled oxygen was used as a material for generating ozone, which was guide and injected into a teat orifice belonging to a milk area suffering from mastitis, of breasts consisting of two milk areas, of Holstein cow suffering from acute mastitis. Ozone discharged from the ozone generator was guided into the teat orifice by use of a guide tube having a length enough to completely isolate the ozone from the exterior, and then was injected through the teat orifice by way of an ozone injection nozzle. The amount of the ozone to be injected thereinto was to such an extent as to be able to fully raise the pressure within the breast to expand milk vessels located at deep regions of the breast, in other words, to such an extent that the injection causes an expansion of the breast and the ozone reaches beneath the skin embracing the mammary gland tissue so as to allow the operator to recognize as a subcutaneous emphysema from a direct contact.

The ozone injected cow by no means complained of a pain and the operation was complete in extreme safety. After the completion of injection, the breast was left to stand to be sensitized to the ozone until the next milking.

In this manner, nine cows suffering from mastitis underwent the ozone treatment, and as a control four cows was subjected to a conventional treatment taking antibiotics. The respective therapeutic effects were observed with time and compared with each other.

Referring to FIG. 5, there is depicted an average number of times of treatment when the treatment was executed in accordance with the respective methods. The conventional treatment method taking antibiotics required 5.3 days for treatment in average, whereas the treatment of the ozone injection method of the present invention was complete in 1.1 days in average. More specifically, eight of nine cows subjected to ozone injection were cured of mastitis by first treatment and there was no need for disposal of milk due to remaining agent. In the case of cows subjected to the treatment taking antibiotics, the resultant milk continued to be disposed of during and even after the period of treatment due to remaining agent.

Reference is made to FIG. 6 which shows processes of treatment in accordance with the two methods. Clinical symptoms were represented by points for comparison. The therapeutic effects of ozone injection in accordance with the present invention were significantly superior to the therapeutic effects of the conventional antibiotics. More specifically, the symptoms of the treatment group taking antibiotics tended to again take a turn for the worse after the seventh day when the treatment was complete, whereas for the treatment group using ozone there was remarkably observed a reduction or relief in swelling or itching of the breast, advantageously making satisfactory improvement in symptoms as a result of processing of productive toxin or free radicals which may give birth to inflammations.

FIG. 7 shows transitions of activity values of NAGase (N-acetyl-beta-D-glucosaminidase) within milk in the process of treatment in the two treatment method, the NAGase being an index for the extent of damage of breast tissues among the qualities of milk. The NAGase active value in milk of the breast subjected to the conventional treatment taking antibiotics has remarkably risen after the treatment, with apparently unstable transition. This revealed that the tissue has been significantly damaged due to tissue irritant properties of the antibiotics themselves which were intrinsically used for treatment. On the contrary, the breast subjected to ozone for treatment has showed a NAGase active value within milk having a very slightly varying transition with a stable and gentle reduction. It was thus evident that the injected ozone itself hardly irritated the tissue of breast.

It was therefore proved that the execution of the ozone injection treatment method would remarkably reduce the number of times of treatment, while simultaneously ensuring the therapeutic effects similar or superior to the conventional method.

Also, in terms of non-irritancy to the breast tissues under treatment, the ozone was significantly superior since it contributes to oxidization and detoxication of toxin, innocuous free radicals and improvement in its spontaneous curing abilities.

As is apparent from the results of the above clinical tests, the cow's mastitis treatment method of the present invention and the apparatus for use in the method have proved to be fully and securely practical from the clinical standpoint.

Referring to FIG. 8, there is depicted another embodiment of the ozone injecting apparatus which comprises an oxygen supplier 31; an ozone generator 32 intended to receive oxygen from the ozone supplier 31 to generate ozone gas, the ozone generator 32 having the same construction as the ozone generator of FIG. 1 described hereinabove; a valve 33 disposed on a piping joining the oxygen supplier 31 and the ozone generator 32; a flow passage 34 from which the ozone generated by the ozone generator 32 is delivered; a flow rate control valve 35 disposed in the flow passage 34 for the control of the flow rate of the ozone to be injected into the cow's breast; a discharge control valve 36 connected to the flow passage 34 for discharging surplus ozone to the exterior; an ozone guide tube 37 connected to the flow rate control valve 35 in the flow passage 34, the tube 37 being equivalent to the guide tube 13 of FIG. 1; an ozone injection nozzle 38 fitted to the tip of the ozone guide tube 37 for injecting the ozone into the cow's breast 39, the nozzle 38 being equivalent to the injection nozzle 14 of FIGS. 2 and 3; and a pressure detector 40 disposed in the ozone delivery tube 37 for detecting a pressure of ozone which has been injected into the cow's breast 39.

FIG. 9 illustrates a further embodiment of the ozone injecting apparatus which further comprises an ozone decomposer 41 connected to the discharge control valve 36. FIG. 10 illustrates a still further embodiment of the ozone injecting apparatus which further comprises a check valve 42 interposed in the ozone guide tube 37 between the pressure detector 40 and the ozone injection nozzle 38.

The pressure detector 40 of FIGS. 8 to 10 is associated with the flow rate control valve 35 and the discharge control valve 36, so that when the pressure of ozone injected into the breast 39 reaches a predetermined level, the flow rate control valve 35 is closed and the discharge control valve 36 is opened to allow surplus ozone from being discharged from the discharge control valve 36 to the exterior. If the ozone decomposer 41 is connected to the discharge control valve 36, the excessive ozone is decomposed and converted into oxygen by the ozone decomposer 41. As shown in FIG. 9, connection of the ozone decomposer 41 to the discharge control valve 36 will allow the surplus ozone to be decomposed and converted into oxygen by the ozone decomposer 41 and then to be discharged. Also, as shown in FIG. 10, due to the presence of the check valve 42 in the ozone guide tube 37 between the pressure detector 40 and the ozone injection nozzle 38, milk existing within the mammary cistern is prevented from flowing backward when the flow rate control valve 35 is closed, eliminating a risk to contaminate the interior of the ozone guide tube 37.

It is to be appreciated that use of solenoid valves as the valves in the apparatus of the present invention would enable the introduction and discharge of the ozone to be automatized, to significantly facilitate the operation of the ozone generator apart from the cow.

In the case of ozone injection by use of the apparatuses of FIGS. 8 to 10, when the pressure of the ozone injected into the breast 39 gradually increases and finally reaches a predetermined level and the pressure detector 40 detects this, the flow rate control valve 35 is closed while the discharge control valve 36 is opened to complete the injection of ozone into the breast 39, the ozone derived from the ozone generator 32 being fed through the discharge control valve 36 into the ozone decomposer 41 in which the ozone is converted into harmless oxygen and discharged to the exterior.

The injection of ozone into the cow's breast as described above will ensure an effective exposure to ozone of the infected milk 22 residing within the mammary cistern 21 shown in FIG. 4. Furthermore, the mammary alveolus 24 of the milk vessels 23 located at deep regions can be fully expanded to thereby allow the ozone to reach the mammary gland cells 25 at the deepest regions while simultaneously urging the inflammation products or the infected milk 22 to be discharged. This will enable domestic animals such as cows to be satisfactorily treated for mastitis.

According to the thus configured ozone injecting apparatus for treating cow's mastitis of the present invention, ozone can be extremely simply and safely injected through the teat orifice into the mastitis, to thereby eliminate a need to use a conventional expensive agent as well as ensuring a full and secure therapeutic effect. It would also be possible to remarkably reduce the period of treatment as compared with the conventional treating method and to omit costly and time-consuming diagnostic technique to thereby eliminate a need for a much expenditure and a high technique which was required for the treatment and diagnosis.

By making use of pressure of the oxygen cylinder or the air compressor, upon a treatment, ozone is injected and reaches mammary gland cellular tissues at the deep regions of the milk areas to be treated. Since the oxygen can thus reach the deep regions of the breast, a high therapeutic effect is achieved. The above-described ozone also serves to oxidize the productive toxin of the infected microbes and react with the free radicals in the inflaming tissues to easily make it innocuous. Furthermore, since the ozone supplies oxygen to the inflaming tissues, spontaneous curing abilities can be enhanced without harming any breast tissues.

On the other hand, in the treatment using the apparatus of the present invention, there is no fear to allow resistance bacteria and superinfection to occur, and no remainder exists in the products, resulting in no loss which would otherwise be caused by the antibiotics remaining in the conventional treatment. Also, safety is secured during the treating operation, making it possible to use it without choosing a person and a time to carry out the treatment.

The present invention also employs the pressure detector arranged in the ozone guide tube for detecting a detector arranged in the ozone guide tube for detecting a pressure of ozone injected into the breast of a cow, whereby on the basis of the detection value of the pressure detector, the injection of ozone is ceased and the ozone from the ozone generator is converted into oxygen and thereafter discharged to the outside, to ensure an ozone injection under an appropriate pressure.

Moreover, due to the presence of the check valve in the ozone guide tube, milk reservoiring within the mammary cistern can be prevented from flowing backward when the flow rate control valve is closed, thereby eliminating a risk that the infected milk may contaminate the interior of the ozone guide tube.

It should be particularly understood that the specific forms of the present invention herein illustrated and described are intended to be representative only, as certain changes or modifications may be made therein without departing from the clear teaching of the disclosure. Accordingly, reference should be made to the following appended claims in determining the full scope of the invention.

What is claimed is:

1. A method of treating domestic animals such as cows for mastitis, comprising the step of:

injecting ozone through a teat orifice of a breast into the interior of the breast.

2. An ozone injecting apparatus for breasts of domestic animals such as cows, comprising:

an ozone generator connected to an oxygen cylinder or an air compressor;

an ozone guide tube for guiding ozone generated by said ozone generator; and an ozone injection nozzle fitted to the tip of said guide tube and intended to be inserted into a teat orifice.

3. An ozone injecting apparatus for breasts according to claim 2, wherein said ozone injection nozzle is a hollow pipe having a diameter allowing an insertion into said teat orifice of domestic animals such as cows, said hollow pipe having at its distal end portion a multiplicity of minute ozone jet orifices.

4. An ozone injecting apparatus for breasts, comprising:

an ozone generator connected to an oxygen cylinder or an air compressor and including a gas flow passage; and a switching valve disposed in said gas flow passage, said switching valve being associated with an ozone decomposer and an ozone guide tube, said guide tube having at its tip an ozone injection nozzle intended to be inserted into a teat orifice of a cow.

5. An ozone injecting apparatus according to claim 4, wherein said switching valve is further associated with an ozone analyzer for automatically measuring and displaying a density of ozone generated by said ozone generator.

6. An ozone injecting apparatus according to claim 4, wherein prior to generation of ozone, said ozone generator flows a material gas for a predetermined duration to discharge air remaining within said generator and said gas guide tube.

7. An ozone injecting apparatus according to claim 4, wherein said ozone generator includes a discharge electrode made of a material such as glass, quartz, ceramics or a metal coated with ceramics to suppress a generation of metal ions and metal dusts.

8. An ozone injecting apparatus according to claim 4, wherein said ozone injection nozzle is a hollow pipe having a diameter allowing an insertion into a teat orifice of a cow, said pipe having at its distal end a multiplicity of minute ozone jet orifices.

9. An ozone injecting apparatus according to claim 4, wherein said ozone injection nozzle is a hollow pipe having a diameter allowing an insertion into a teat orifice of a cow, said pipe having at its distal end a gas filter for jetting ozone.

10. An ozone injecting apparatus according to claim 4 wherein the gas volume of ozone and oxygen to be injected into a breast at a time is 0.1 to 0.3 liter and the density of ozone is 1 to 50 mg $O^3$/liter.

11. An ozone injecting apparatus for cow's breasts, comprising:

an oxygen supplier;

an ozone generator for receiving oxygen supplied from said oxygen supplier to generate ozone and for discharging said ozone, said ozone generator including an ozone delivery flow passage;

a flow rate control valve disposed in said ozone delivery flow passage for controlling the flow rate of ozone;

a discharge control valve disposed in said ozone delivery flow passage for discharging surplus ozone to the outside;

an ozone guide tube coupled to said flow rate control valve and having at its tip an ozone injection nozzle for injecting ozone into a cow's breast; and a pressure detector disposed in said ozone guide tube for detecting a pressure of ozone injected into said cow's breast;

said flow rate control valve being controlled on the basis of a detection value of said pressure detector so as to discharge surplus ozone through said discharge control valve.

12. An ozone injecting apparatus for cow's breasts according to claim 11, further comprising:

an ozone decomposer coupled to said discharge control valve disposed in said ozone delivery flow passage, said ozone decomposer serving, when a pressure detected by said pressure detector exceeds a predetermined level, to allow surplus ozone to flow thereinto and to be converted into oxygen.

13. An ozone injecting apparatus for cow's breasts according to claim 11 further comprising:

a check valve disposed in said ozone guide tube short of said ozone injection nozzle.

* * * * *